United States Patent
Welch et al.

(10) Patent No.: US 9,833,386 B2
(45) Date of Patent: Dec. 5, 2017

(54) METHOD OF, AND SYSTEM FOR SMOOTHING TEETH

(71) Applicants: James D. Welch, Omaha, NE (US); Janet M. Wehrli, Omaha, NE (US)

(72) Inventors: James D. Welch, Omaha, NE (US); Janet M. Wehrli, Omaha, NE (US)

( * ) Notice: Subject to any disclaimer, the term of this patent is extended or adjusted under 35 U.S.C. 154(b) by 0 days.

(21) Appl. No.: 14/756,809

(22) Filed: Oct. 17, 2015

(65) Prior Publication Data
US 2017/0105906 A1    Apr. 20, 2017

Related U.S. Application Data

(63) Continuation of application No. 14/121,414, filed on Sep. 3, 2014, which is a continuation of application No. 12/380,972, filed on Mar. 9, 2009, which is a continuation of application No. 11/505,167, filed on Aug. 16, 2006.

(60) Provisional application No. 60/787,145, filed on Mar. 30, 2006, provisional application No. 62/282,756, filed on Aug. 11, 2015.

(51) Int. Cl.
*A61K 6/087* (2006.01)
*A61K 6/06* (2006.01)
*A61K 6/027* (2006.01)
*A61K 6/00* (2006.01)

(52) U.S. Cl.
CPC .......... *A61K 6/0668* (2013.01); *A61K 6/0017* (2013.01); *A61K 6/0047* (2013.01); *A61K 6/027* (2013.01); *A61K 6/087* (2013.01)

(58) Field of Classification Search
CPC .......... A61C 17/00; A61C 17/16; A61C 17/22; A61K 6/0668; A61K 6/027; A61K 6/087

USPC .................................................. 433/215, 216
See application file for complete search history.

(56) References Cited

U.S. PATENT DOCUMENTS

| | | | |
|---|---|---|---|
| 4,148,872 A | 4/1979 | Wagenknecht et al. | 424/48 |
| 4,150,112 A | 4/1979 | Wagenknecht et al. | 424/48 |
| 4,156,715 A | 5/1979 | Wagenknecht et al. | 424/48 |
| 4,159,315 A | 6/1979 | Wagenknecht et al. | 424/48 |
| 4,161,517 A | 7/1979 | Wagenknecht et al. | 424/48 |
| 4,225,579 A | 9/1980 | Kleinberg | 424/48 |
| 4,229,485 A | 10/1980 | Brown et al. | 426/305 |
| 4,397,837 A * | 8/1983 | Raaf | A61K 8/19 424/51 |
| H83 H | 7/1986 | Poletto et al. | 424/49 |
| 5,249,570 A | 10/1993 | Cox | 128/206.28 |
| 5,405,836 A | 4/1995 | Richar et al. | 514/23 |
| 5,455,024 A | 10/1995 | Winston et al. | 424/52 |
| 5,693,334 A | 12/1997 | Miskewitz | 424/440 |
| 5,944,516 A | 8/1999 | Deshaies | 433/1 |

(Continued)

OTHER PUBLICATIONS

Menal, Orauet "Plague prevention is key".
G.C. America, MI Paste.

*Primary Examiner* — Nicholas Lucchesi
*Assistant Examiner* — Drew Folgmann
(74) *Attorney, Agent, or Firm* — James D. Welch

(57) ABSTRACT

A method of smoothing teeth is disclosed that is based on surprising evidence achieved by practicing a method involving application of calcium powder or calcium containing composition to teeth, and maintaining it in contact with the teeth by application of an edible adherent wax containing material, that serves to maintain contact between the teeth and the calcium powder or calcium containing composition for at least one hour.

4 Claims, 4 Drawing Sheets

SMOOTHER

(56) References Cited

U.S. PATENT DOCUMENTS

| | | | |
|---|---|---|---|
| 5,993,786 A | 11/1999 | Chow et al. | 424/49 |
| 6,014,950 A | 1/2000 | Rogers | 119/710 |
| 6,050,224 A | 4/2000 | Owens | 119/710 |
| 6,309,676 B1 | 10/2001 | Lewandowski | 424/754 |
| 6,322,772 B1 | 11/2001 | Wehrli | |
| 6,405,681 B1 | 6/2002 | Ward | 119/707 |
| 6,441,354 B1 | 8/2002 | Seghatol et al. | |
| 6,475,471 B1 | 11/2002 | Wehrli | |
| 6,509,007 B2 | 1/2003 | Rajaiah et al. | 424/53 |
| 6,610,276 B2 | 8/2003 | Melman | 424/57 |
| 6,649,147 B1 | 11/2003 | Ye et al. | 424/49 |
| 6,669,928 B1 | 12/2003 | Gurol | 424/49 |
| 6,685,971 B2 | 2/2004 | Xu | 424/725 |
| 6,827,041 B2 | 12/2004 | Hague et al. | 119/709 |
| 6,886,497 B1 | 5/2005 | Hague | 119/710 |
| 6,905,673 B2 | 6/2005 | Rajaiah et al. | 424/49 |
| 6,997,708 B2 | 2/2006 | Allred et al. | 433/80 |
| 7,013,838 B2 | 3/2006 | Hague | 119/710 |
| 7,022,314 B2 | 4/2006 | Barabolak et al. | 424/48 |
| 7,029,690 B1 | 4/2006 | Wehrli | |
| 7,955,591 B1 * | 6/2011 | Wehrli | A61C 19/063 424/49 |
| 8,658,139 B1 | 2/2014 | Cutler | |
| 2003/0113276 A1 * | 6/2003 | Rajaiah | A61C 19/063 424/49 |
| 2003/0124230 A1 | 7/2003 | Zielinski | |
| 2003/0175326 A1 | 9/2003 | Thombre | |
| 2003/0206948 A1 | 11/2003 | Gergely et al. | |
| 2004/0057910 A1 * | 3/2004 | Lee | A61K 8/22 424/53 |
| 2004/0101493 A1 | 5/2004 | Scott et al. | |
| 2004/0101494 A1 | 5/2004 | Scott et al. | |
| 2004/0110111 A1 * | 6/2004 | Wasylucha | A61C 19/063 433/29 |
| 2004/0118360 A1 | 6/2004 | Hague et al. | |
| 2004/0141960 A1 * | 7/2004 | Hberlein | C12Q 1/32 424/94.4 |
| 2004/0244720 A1 | 12/2004 | Jia | |
| 2005/0008584 A1 | 1/2005 | Montgomery et al. | |
| 2005/0071927 A1 | 4/2005 | Hague et al. | |
| 2006/0088482 A1 | 4/2006 | Wulknitz et al. | |
| 2006/0153935 A1 * | 7/2006 | Blahut | A61K 31/60 424/735 |
| 2007/0298003 A1 * | 12/2007 | Chandra | A61K 8/60 424/70.12 |
| 2010/0150974 A1 * | 6/2010 | Butler | A61K 8/24 424/401 |

* cited by examiner

METHOD OF, AND SYSTEM FOR SMOOTHING TEETH

TECHNICAL AREA

The present invention relates to repair of teeth, and more particularly to method of smoothing teeth by, for instance, filling in cracks, chips and erroded areas by applying calcium thereto and maintaining it in contact therewith by application of a composition of matter that adheres to said teeth.

BACKGROUND

Attorney Welch has been acting as Attorney for Co-inventor and Client, Janet M. Wehrli regarding Patent efforts regarding oral treatments for many years. The latest of said inventions being subject in application Ser. No. 14/121,414, which relates to means for controlling plaque on teeth, and more particularly to a method involving application of a composition of material to teeth and gums. The invention in application Ser. No. 14/121,414 was first described in the Parent Applications Nos. 12/380,972, 11/505,167 and 60/787,145 and is a method of controlling plaque on teeth which comprises the basic steps of providing a system comprising means for containing a composition of material which:
   adheres to teeth and serves as a barrier between teeth and gums, and the environment; inhibits plaque from adhering to teeth; and optionally dissolves and/or absorbs plaque.
Said system can further serve to neutralize acids and freshen breath.

Attorney Welch has, over the years, experimented with various dental maintenance matters personally and has developed some novel approaches thereto, some of which are disclosed herein. In keeping with his researcher orientation, he recently conceived and practiced the invention disclosed herein to the end of achieving a very unexpected result. Co-Inventor Wehrli has expressed great surprise at what she has observed regarding the lower edges of Attorney Welch's Upper. Frontal, and Upper edges of his Lower Frontal teeth. Attorney Welch mentioned to her that he had been practicing a method that had resulted in said "edges" becoming far "smoother" than they had been when he ran his tongue thereover. That is, they seem to have been recalcified. Co-Inventor Wehrli has a long background in the oral care industry, and upon observing Attorney Welch's teeth, expressed that what she saw was not expected. There was definite evidence of renewed calcification, eg. remineralization of enamel. As Attorney Welch has included a composition of matter that Co-Inventor Wehrli developed in his research, she is included as Co-Inventor in this effort.

A Computer Search of Patents provided:
   a) Using Recalcify Teeth and beeswax—no hits;
   b) Using Recalcify. Teeth and Sodium Bicarbonate—one hit:
      Patent to Wehrli No. 7,955,591.
Further, a Patent to Cuther, U.S. Pat. No. 8,658,139 is mentioned as it describes preventing tooth decay using Calcium Carbonate having a particle size of 1-100 nanometers.

And, a Patent to Seghatol et al., U.S. Pat. No. 6,441,354 is mentioned as it provides insight that known approaches to improving teeth are use of prosthetics, filling dental caries and application of caps.

It is also mentioned that a product that goes by the name "MI" Paste is milk calcium based, and is used by Dental practitioners to recalcify teeth by a burnishing approach.

Also disclosed are Patent to Inventor Wehrli:
   U.S. Pat. Nos. 7,955,591; 7,029,690; 6,475,471 and 6,322,772.
And, references identified by the Examiner are:
Patent to Raaf et al., U.S. Pat. No. 4,397,837; and
Published Applications by Rajaiah et al., No. 2003/0113276; and
Lee et al., No. 2004/0057910 in fashioning a Section 103 rejection.
The Raaf et al. 836 Patent describes sequential application of two material phases, each containing different ingredients, namely, in either order of application, 1) water soluble calcium and 2) water soluble phosphate. There is no indication what-so-ever that only one phase should be applied, directly followed by application of an anderent material which serves to maintain contact of the contents of said one phase with teeth for a prolonged period of time. Rather, the two phases are applied sequentially so that ions in each are caused to be successively absorbed into dental enamel with the result that rehardening of demineralized areas in dental enamel are rehardened. This is summarized in Col. 2, Lined 28-38 in Raaf et al. 837. The present invention involves applying only one phase which comprises calcium, (and perhaps, sikultaneously, other materials), followed directly by applying a composition of matter that provides an adhesion property that keeps the composition in contact with teeth.

The 276 Published Applications by Rajaiah et al., requires that to maintian contact between a composition and teeth, a Dental Strip is required. A Dental Strip is not required by the present invention.

The Lee et al. 910 Published Application mentuions use of Beeswax as an adhesion providing material.

Need remains for methodology and supporting systems that when practiced cause a smoothing of teeth.

DISCLOSURE OF THE INVENTION

The present invention is a method of smoothing teeth comprising the steps of:
   a) optionally surface cleaning at least one tooth to be smoothed;
   b) apply a calcium containing composition of matter to said area of said at least one tooth, said composition of matter serving to retain said calcium in place;
   c) maintaining the scenario achieved in the foregoing steps for at least one hour.
Said method can involve using a composition of matter that comprises:
   ⅛ beeswax;
   ⅝ oil; and
   ⅖ plaque inhibiting material;
said composition of matter being optionally further comprised of an amount of powdered calcium equal to between 1 and 100% by volume of a volume of the recited composition.
(It is noted that a suitable powdered calcium in any methodology of the present invention is available from NutraBio as Ecopure Okinawan Coral Calcium).

The present invention is further a method of smoothing teeth comprising the steps of:
   a) optionally surface cleaning at least one tooth to be smoothed;

b) topically apply calcium powder or calcium containing composition to the area on said at least one tooth that is to be smoothed;
c) apply a composition of matter to said area of said at least one tooth that has had calcium powder or calcium containing composition applied thereto, said composition of matter serving to retain said calcium powder in place;
d) maintaining the scenario achieved in the foregoing steps for at least one hour.

It is noted that Applicant Welch has found that the method works best when practiced at night while sleeping. The results the following morning are noticably stable. Therefore, the period of application can greatly exceed one hour, without any noticable untoward effects occuring.

Said method can involve that the steps of:
b) topically apply calcium powder or calcium containing composition to the area on said at least one tooth that is to be smoothed;
c) apply a composition of matter to said area of said at least one tooth that has had calcium powder or calcium containing composition applied thereto, said composition of matter serving to retain said calcium powder in place;

are accomplished substantially simultaneously by providing said composition of matter in a tube or equivalent, exposing said composition of matter to powdered calcium by dipping it thereinto, and applying the combined calcium powder and composition of matter to said at least one tooth in a single effort which substantially maintains the order of application of calcium powder and composition of matter.

Said method can involve that the at least one tooth is present in the mouth of a human, and the optional step of surface cleaning said at least one tooth is and can involve surface cleaning all teeth present in said human mouth, by a method such as:
1) swishing hydrogen peroxide around in the human's mouth for at least one minute before spitting it out;
2) preparing a toothbrush by first dampening it with water, then applying a spurt of hand sanitizer thereto, followed by applying some triple antibiotic ointment thereto, followed by dipping said toothbrush into Epsom Salts, followed by dipping said toothbrush into sodium bicarbonate; optionally applying a small amount of toothpaste, (eg. Sensodyne Anti-Plaque), and then brushing said at least one human tooth with said so prepared toothbrush;
3) before spitting the results of practicing step b) out, swishing said results of practicing step b around in said human mouth for at least 15 minutes;
4) spitting out the remaining results of practicing step b) out.

Said method can involve that step b) involves powdered Coral Calcium.

Said method can involve that the step c) composition of matter comprises Beeswax.

Said method can involve the step c) composition of matter comprises at least one selection from the group consisting of:
beeswax;
honey;
gum;
lanolin;
tallow;
carnuba;
candelilla;
soy;
ceresin;
montan;
paraffin;
ethylenic polymers;
chlorinated naphthalenes;
Fisher-Tropsch;
castor wax;
glycowax;
carnuba wax.

Said method can involve that the step c) composition of matter comprises at least one selection from the group consisting of an oil comprising at least one selection from the group consisting of:
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
seseme oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil;
rapeseed oil;
cod oil.

Said method can involve that the step c) composition of matter comprises a selection from the group consisting of:
⅛ beeswax;
⅝ oil; and ⅔ plaque inhibiting material; and
⅛ beeswax;
⅝ oil; and
⅔ plaque inhibiting material;
said composition of matter being further comprised of an amount of powdered calcium equal to between 1 and 100% by volume of a volume of the recited composition.

(It is also noted that Step b) can involve a composition of calcium and a material that adheres to teeth).

Said method can involve that the plaque inhibiting material selected from the group consisting of:
sodium bicarbonate; and
potassium bicarbonate; and
other buffering salt.

Said method can involve the composition of matter comprises at least one selection from the group consisting of:
oils;
fragrances;
preservatives;
flavoring;
colorings;
medicinals; and
decay inhibiting materials.

Said method can involve that the composition of matter provides negative ions when warmed in a typical mamallian's mouth will cause the effect.

Said method can involve that the composition of matter:
adheres to teeth and serves as a barrier between teeth and gums, and the environment;
inhibits plaque from adhering to teeth; and
optionally dissolves and/or absorbs plaque.

Said method can involve the step of applying said step c) composition of matter to said teeth via:
application from a Chap-Stick type tube of material;
application from a stick of material;
application by use of finger;
application by use of an applicator held by fingers;
application via a spray;
application by syringe; and
application via applying a strip containing said material to said teeth;
application via use of an application brush or the like, as opposed to an toothbrush brush which serves to remove material.

Said method can further comprise use of means for dispensing said step c) composition of matter selected from the group consisting of:
a tube comprising means for dispensing said composition of material onto teeth, said dispensing means comprising a means for causing said material to extend from said tube in a manner allowing it to be placed into contact with teeth;
a tub of composition for application via fingers or the like;
a means for spraying said material at teeth.

Said method can involve the step c) composition of matter is fabricated by a method comprising the steps of:
a) providing an edible wax and heating it until it becomes a liquid;
b) entering a component which serves to inhibit plaque from forming on teeth and causing it to become substantially uniformly distributed therewithin;
c) cooling the result.

Said method can involve that the step c) composition of matter is caused to contain a selection from the group consisting of:
one or more oils;
fragrances;
flavors;
preservatives;
colorings; and
medicinals;
is entered before cooling in step c.

Said method can provide that said composition of material comprises, by volume, a selection from the group consisting of:
approximately:
⅛ edible adherent material, such as beeswax, (one part);
⅝ oil (five parts); and
⅔ plaque inhibiting material (two parts); and
approximately:
⅛ beeswax;
⅝ oil; and
⅔ plaque inhibiting material;
said composition of matter being further comprised of an amount of powdered calcium equal to between 1 and 100% by volume of a volume of the recited composition.

Said method can involve that the ⅝ oil includes medicinals.

Said method can involve repeating it:
at last once a day for at least one week;
at least once a day for at least two weeks;
at least twice a day;
at least twice a day for at least two weeks;
at least once a day for more than two weeks.

Said method can involve that the composition of matter comprises at least one selection from the group consisting of:
almond flavored;
beef flavored;
chicken flavored;
turkey;
lamb flavored;
fish;
liver;
egg;
dairy flavored;
mint;
orange.

Said method can involve the at least one tooth is from a selection form the group consisting of:
cat teeth;
dog teeth; and
human teeth.

Said method can involve the composition of matter contains at least one selection from the group consisting of:
acid neutralizing material;
breath freshening material;
at least one medicinal; and
at least one decay inhibiting material.

Said method can involve that the composition of matter does not require an acid component and presents with a pH of at least 6.0.

A present invention method can provide that the steps of:
b) topically apply calcium powder or calcium containing composition to the area on said at least one tooth that is to be smoothed; and
c) apply a composition of matter to said area of said at least one tooth that has had calcium powder or calcium containing composition applied thereto, said composition of matter serving to retain said calcium powder in place;
are accomplished substantially simultaneously by providing said composition of matter in a tube or equivalent, exposing said composition of matter to powdered calcium by dipping it thereinto, and applying the combined calcium powder and composition of matter to said at least one tooth in a single effort which substantially maintains the order of application of calcium powder and composition of matter.

A present invention method can provide that the steps of:
b) topically apply calcium powder or calcium containing composition to the area on said at least one tooth that is to be smoothed; and
c) apply a composition of matter to said area of said at least one tooth that has had calcium powder or calcium containing composition applied thereto, said composition of matter serving to retain said calcium powder in place;

are accomplished substantially simultaneously by providing said composition of matter and calcium powder or calcium containing composition in a strip, and applying the combined calcium powder or calcium containing composition and composition of matter to said at least one tooth in a single effort by applying said strip thereto, in a manner that substantially maintains the order of application of calcium powder or calcium containing composition and composition of matter.

A present invention method of smoothing teeth can comprise the steps of:
a) optionally surface cleaning at least one tooth to be smoothed;
b) apply a composition of matter to said area of said at least one tooth that contains calcium powder or calcium containing composition, said composition of matter serving to retain said calcium powder or calcium containing composition in place;
d) maintaining the scenario achieved in the foregoing steps for at least one hour.

Said method can provide that the composition of matter that comprises, approximately:
⅛ beeswax;
⅝ oil; and
⅖ plaque inhibiting material;
also further comprises an amount of powdered calcium equal to between 1 and 100% by volume of a volume of the recited composition.

Another present invention method provides that the steps of:
b) topically apply calcium powder or calcium containing composition to the area on said at least one tooth that is to be smoothed; and
c) apply a composition of matter to said area of said at least one tooth that has had calcium powder or calcium containing composition applied thereto, said composition of matter serving to retain said calcium powder or calcium containing composition in place;

are accomplished by providing said composition of matter substantially without calcium powder present therein and composition of matter substantially with calcium powder present therein in a tube, said composition of matter substantially with calcium powder present therein being present at a selection from the group consisting of:
at a central location therewithin; and
surrounding said central location therewithin;
with said composition of matter substantially without calcium powder present therein being present at the complimentary position of:
surrounding said central location therewithin;
a central location therewithin.

The method continues with and first causing said composition of matter containing calcium to be applied to said at least one tooth, followed by causing said compositing of matter not containing calcium to be applied to said at least one tooth in quick succession.

A modified version of the method just recited can involve the steps of:
b) topically apply calcium powder or calcium containing composition to the area on said at least one tooth that is to be smoothed; and
c) apply a composition of matter to said area of said at least one tooth that has had calcium powder or calcium containing composition applied thereto, said composition of matter serving to retain said calcium powder or calcium containing composition in place;

being accomplished by providing said composition of matter substantially without calcium powder present therein and composition of matter substantially with calcium powder present therein in a tube, said composition of matter substantially with calcium powder present therein being present at a selection from the group consisting of:
on a first side of a diameter location therewithin; and
on a second side of said diameter location therewithin;
with said composition of matter substantially without calcium powder present therein being present at the complimentary position of:
on said second side of said diameter location therewithin;
on said first side of a diameter location therewithin.

The method continues with and first causing said composition of matter containing calcium to be applied to said at least one tooth, followed by causing said compositing of matter not containing calcium to be applied to said at least one tooth in quick succession.

It is also noted that negative limitations can, but not necessarily, include that the preferred embodiment of the present invention does not involve use of garlic, charcoal, zinc, zinc oxide, sodium percarbonate, brushes, abrasive agents for their abrasive properties, ice, hemoglobin, oxygen, glycerin, acetic acid, citrus acid, vitis acid, (no strong acid is involved in any formulation of the present invention), peanut oil, polybutene, chewing gum, surfactants, emulsifiers, triclosan, removable backing strips, toothpastes, chewable toys, polymers, hexametaphosphate, xylitol etc. These, and other extraneous materials or compositions of matter and practices are identified in various cited prior art. The present invention functions by providing a barrier between teeth and an oral environment for a period of at least an hour. Any material or compositions of matter or practice not required to cause said "barrier" effect and includes a plaque inhibiting and/or reducing or other agent which reduces adherence to teeth is not required by the present invention. Such exclusions as just exemplified are simply not present in the preferred embodiment of the present invention. Neither present in the present invention method is a requirement for removal of the barrier forming agent in the present invention, although optional removal can be practiced, at some time, for aesthetic purposes.

The present invention also comprises a system for containing a composition of matter substantially without calcium powder present therein and a composition of matter substantially with calcium present therein, said system comprising a tube, said composition of matter substantially with calcium present therein being present at a selection from the group consisting of:
on a first side of a diameter location therewithin; and
on a second side of said diameter location therewithin;
with said composition of matter substantially without calcium present therein being present at the complimentary position of:
on said second side of said diameter location therewithin;
on said first side of a diameter location therewithin.

A present invention also comprises a system for containing a composition of matter substantially without calcium present therein and a composition of matter substantially with calcium present therein, said system comprising a tube, said composition of matter with calcium present therein being present at a selection from the group consisting of:
   at a central location therewithin; and
   surrounding said central location therewithin;
with said composition of matter substantially without calcium present therein being present at the complimentary position of:
   surrounding said central location therewithin;
   a central location therewithin.
In both cases, in use, a user first causes said compositing of matter containing calcium to be applied to at least one tooth, followed by causing said compositing of matter not containing calcium to be applied to said at least one tooth.

In the foregoing and throughout this Application, it is to be understood that the composition of matter preferably comprises, but is not limited to approximately:
   ⅛ beeswax;
   ⅝ oil; and
   ²⁄₈ plaque inhibiting material.
A calcium containing composition also further comprises an amount of powdered calcium equal to between 1 and 100% by volume of a volume of the recited composition.

The present invention will be better understood by reference to the Detailed Description Section of this Specification, in conjunction with the Drawings.

BRIEF DESCRIPTION OF THE DRAWINGS

FIG. 8a demonstrates the lower tooth of FIG. 8a with a smoother top edge after practice of the present invention method.

DETAILED DESCRIPTION

Figure 1A:
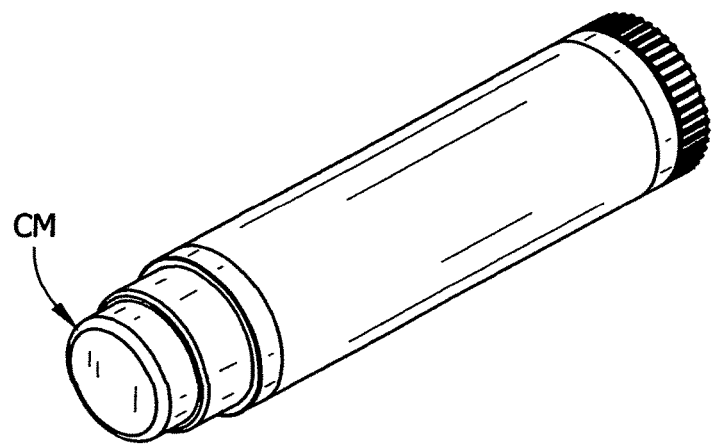
FIG. 1a shows a Chap-Stick type tubular container for composition.

Turning now to FIG. 1a, there is shown a Chap-Stick type tubular container for calcium and composition of matter (CM). This is a preferred embodiment.

Figure 1B:
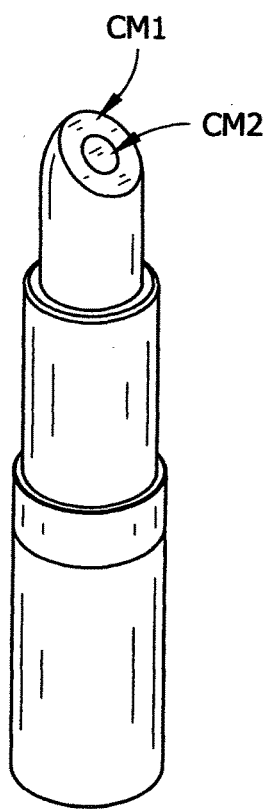
FIG. 1b shows a tubular container containing both calcium containing and substantially not calcium containing compositions of matter, one centrally and one surrounding said central location.

FIG. 1b shows a tubular container as in FIG. 1a, containing both calcium containing (CM1) (CM2) and not necessarily calcium containing (CM2) (CM1) compositions of matter, one centrally located (CM2) and one surrounding said central location (CM1). (Note, the definitely calcium containing composition can be either centrally located, or surrounding the central location).

Figure 1C:
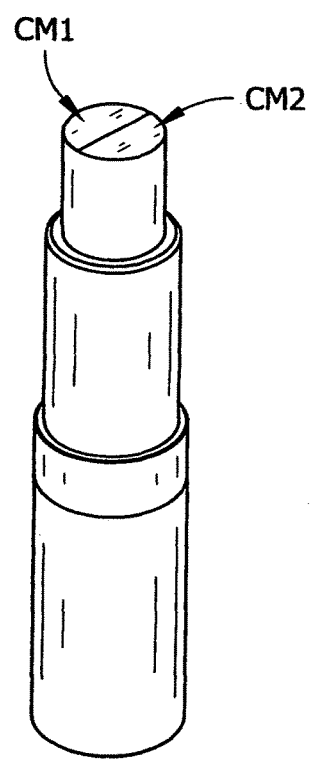
FIG. 1c shows a tubular container containing both calcium containing and substantially not calcium containt compositions of matter, one on one side of a diameter and one on the other side of said diameter.

FIG. 1c shows a tubular container as in FIG. 1a, containing both calcium containing (CM1) (CM2) and not necessarily calcium containing (CM2) (CM1) compositions of matter, one on one side of a diameter (CM1) and one on the other side of said diameter (CM2).

Figure 2:
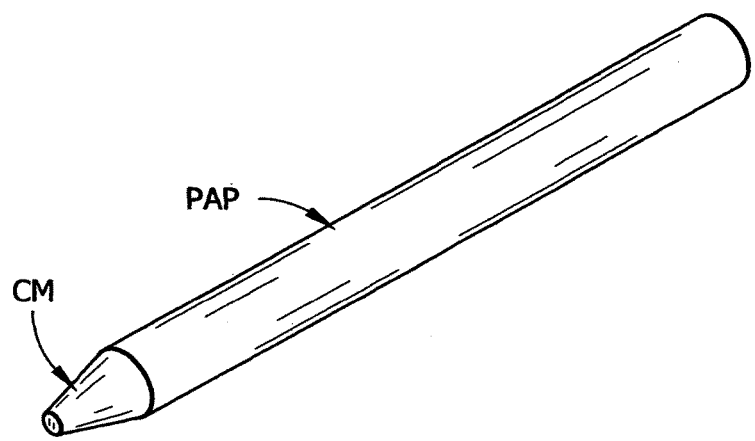
FIG. 2 shows a stick of composition material that can be applied to teeth.

FIG. 2 shows a stick of composition of matter (CM), (calcium containing or not), that can be applied to teeth. Much like a Crayon it preferably has a surrounding paper.

Figure 3:
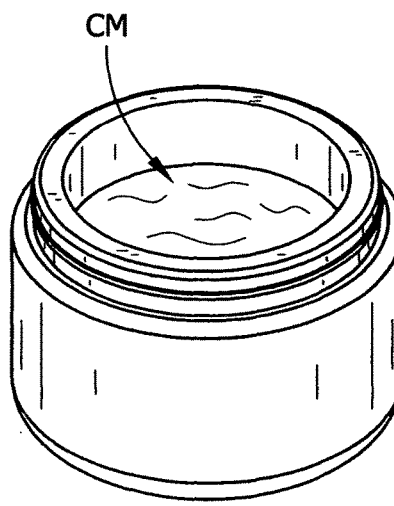
FIG. 3 demonstrates a tub of composition from which a person can apply composition by use of fingers.

FIG. 3 demonstrates a tub of composition of matter (CM) from which a user can apply composition by use of fingers.

Figure 4:
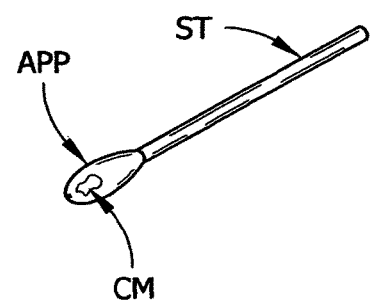
FIG. 4 demonstrates use of an applicator held by fingers to apply composition.

FIG. 4 demonstrates use of an applicator (ST) held by a user's fingers which can be used to apply composition of matter (CM).

Figure 5:
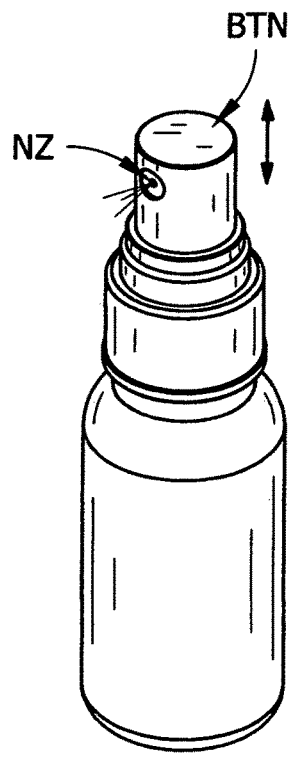
FIG. 5 demonstrates application of composition via a spray.

FIG. 5 demonstrates application of composition of matter (CM) can be via a spray container.

Figure 6:
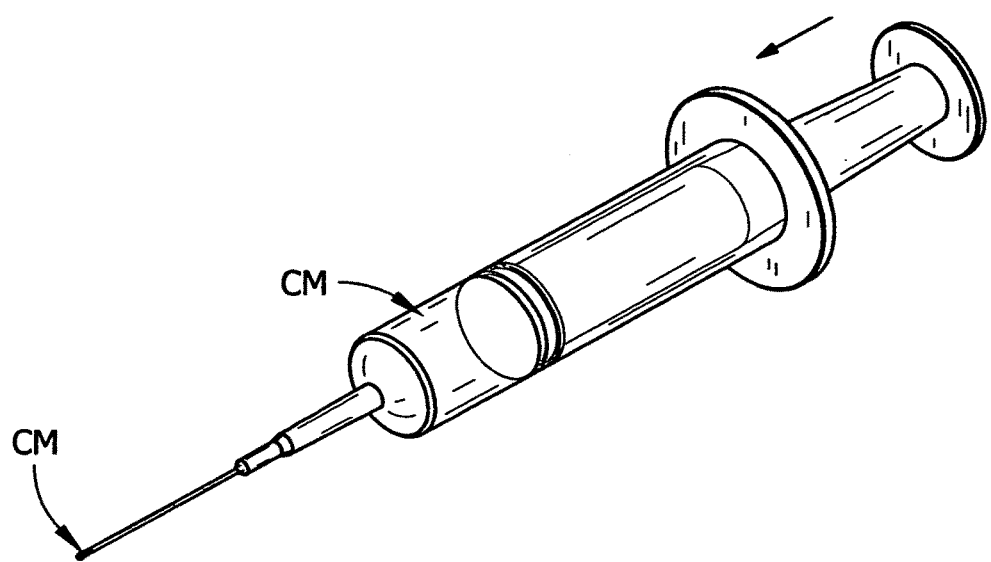
FIG. 6 demonstrates application of composition by syringe.

FIG. 6 demonstrates application of composition of matter (CM) can be by syringe.

It is noted that in the cases of FIGS. 2-6 a user will typically apply calcium, (eg. powdered coral calcium or perhaps by brushing with a calcium containin toothpaste such as Sensodyne Pronamel and swishing it over teeth), to areas of teeth needing smoothing, and then apply composition of matter not necessarily containing calcium, using the respective systems in said FIGS. 2-6.

Figure 7:
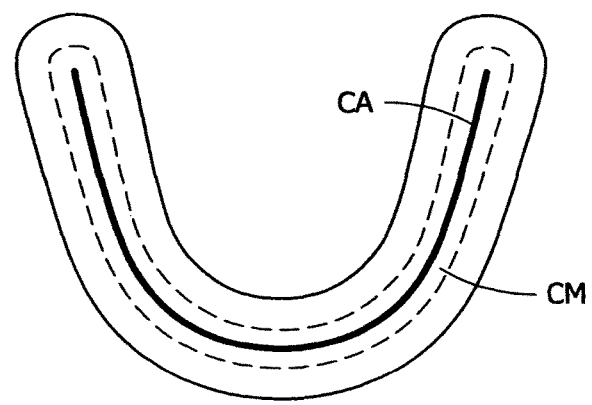
FIG. 7 demonstrates application of composition via applying a strip containing said calcium and composition.

FIG. 7 demonstrates application of composition of matter via applying a strip containing said composition of matter, and calcium, in ascending order so that calcium will directly contact teeth. This is also a preferred approach.

Figures 8A, 8B:
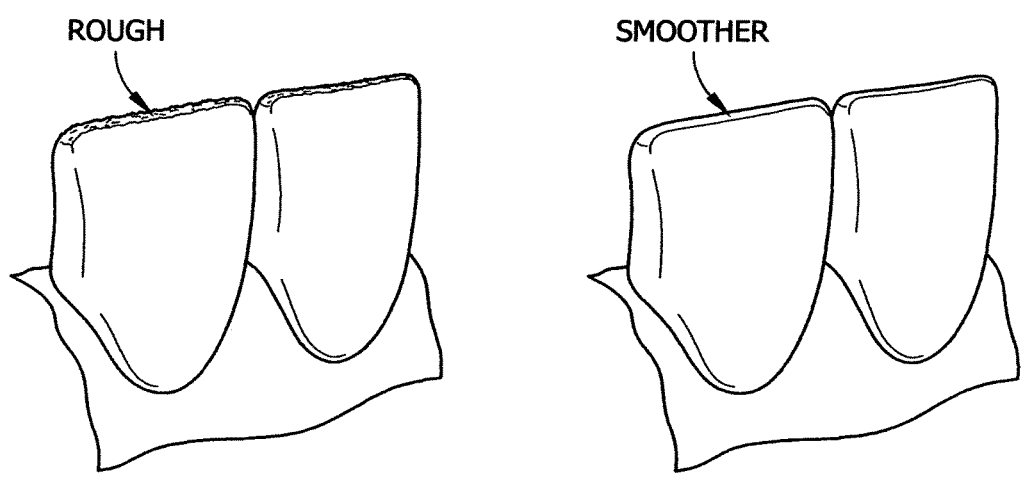
FIG. 8a demonstrates .a lower tooth with rough top edge which contains a "groove", before practice of the present invention.

FIG. 8a demonstrates a lower tooth with rough top edge which contains a "groove", before practice of the present invention.

FIG. 8b demonstrates the lower tooth of FIG. 8a with a smoother top edge after practice of the present invention method or a period of a few weeks. Extended practice of the present invention leads to progressively better results. Note, the results of FIGS. 8a and 8b have been observed and are directly the experience of Applicant Welch. He attests that his teeth have become smoother in regions of the lower edges of upper frontal teeth, and the upper edges of lower frontal teeth. Applicant Welch can only attest to the "tongue" test. His treated teeth feel much smoother when he runs his tongue over them. The way Applicant Welch stumbled onto the present invention involved brushing and swishing Sensodyne ProNamel toothpaste over the rough edged teeth. He noticed over a very long period of time that the roughness of his teeth seemed to be smoothing out. He than began using the composition Applicant Wehrli had earlier developed, as described elsewhere in the Specification, and noticed a faster pace of the roughness being smoothed. Applicant Welch cautiously reported the effect to Applicant Wehrli, but after some time reported that he knew the effect was real. He then began applying powdered Coral Calcium to the rough edges of his teeth, and noticed a much faster pace of the roughness smoothing out. Applicant Welch as been practicing the present invention primarily at night, while sleeping and has also found that results do not brush off in the morning. It appears to Applicant Welch that calcium has been firmly incorporated into rough edges of his teeth. To be completely scientifically correct, Applicant Welch can not attest that "recalcification" is a warranted term at this time, but does attest that a definite smoothing effect has occured on rough edges of his teeth by practice of the present invention. Applicant Wehrli has suggested that the presence of "OH" ions provided by her previously developed composition of matter are necessary for the effect Applicant Welch has discovered.

In any of the foregoing methodology, it is noted that the composition of matter which is applied to maintain calcium in place can itself contain calcium.

Also, while not Claimed as such herein, it is believed that the effect Applicant Welch has discovered is the result of the recalcification of the teeth subjected to the present invention methodology. Formal research would be necessary before such a definite claim of recalcification is justified, however. Initial contact with researchers in the dental field has been achieved, and interest was expressed thereby.

It is also noted that while FIGS. 1b and 1c suggest using a single tube for dispensing both Calcium containing and not necessarily Calcium containing compositions of matter, it is withing the scope of the Claims to use two tubes, one for Calcium containing and one for not necessarily Calcium containing compositions of matter.

It is also noted that very recent investigation of Mr. Welch's teeth suggests that the effect described results from a rebuilding of apparent enamel from location on his teeth which still have enamel present. Observation seems to indicate that the grooves in the tops of his lower front teeth are being compensated by enamel-like material growing up and into the grooves.

Also, it has been noticed that combining Sensodyne Pro-Enamel with Coral Calcium prior to application to teeth seems to improve adherence properties.

Finally, it is possible that the present invention might provide the seeds of a new approach to achieving more than smoothing rough portions of teeth. It might provide insight into a new approach to filling cavities.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of smoothing teeth consisting of the steps:
   a) providing at least one tooth that is to be smoothed;
   b) topically applying calcium powder or calcium containing composition to an area on said at least one tooth that is to be smoothed;
   c) applying a composition of matter consisting of edible adherent wax containing material to said area of said at least one tooth that has had calcium powder or calcium containing composition applied thereto, said composition of matter serving to retain said calcium powder or calcium containing composition in place without requiring use of a backing strip;
   d) maintaining the result of practicing steps a)-c) for a period of time; and
   e) repeating steps b)-d).

2. A method of smoothing teeth consisting of the steps:
   a) providing at least one tooth that is to be smoothed;
   b) topically applying calcium powder or calcium containing composition to an area on said at least one tooth that is to be smoothed;
   c) applying a composition of matter consisting of:
      $1/8$ beeswax;
      $5/8$ oil; and
      $2/8$ plaque inhibiting material;
   wherein the $2/8$ plaque inhibiting material is selected from the group consisting of:
      sodium bicarbonate; and
      potassium bicarbonate;
   to said area of said at least one tooth that has had calcium powder or calcium containing composition applied thereto, said composition of matter serving to retain said calcium powder or calcium containing composition in place without requiring use of a backing strip;
   d) maintaining the result of practicing steps a)-c) for a period of time; and
   e) repeating steps b)-d).

3. A method as in claim 1, in which the step d) period of time is at least one hour.

4. A method as in claim 2, in which the step d) period of time is at least one hour.

* * * * *